United States Patent [19]

Christian et al.

[11] Patent Number: 4,958,642

[45] Date of Patent: Sep. 25, 1990

[54] GUIDE WIRE ASSEMBLY WITH ELECTRICAL FUNCTIONS AND MALE AND FEMALE CONNECTORS FOR USE THEREWITH

[75] Inventors: Jeffrey J. Christian, San Jose; Menahem Nassi, Palo Alto, both of Calif.

[73] Assignee: Cardiometrics, Inc., Mountain View, Calif.

[21] Appl. No.: 411,399

[22] Filed: Sep. 22, 1989

Related U.S. Application Data

[63] Continuation-in-part of Ser. No. 265,909, Nov. 2, 1988.

[51] Int. Cl.$^5$ ................................................ A61B 5/00
[52] U.S. Cl. ...................................... 128/772; 128/657; 604/164; 604/283; 439/448; 439/449; 439/668; 439/825
[58] Field of Search ............... 128/657, 772; 604/95, 604/164, 280, 282, 283; 439/445, 448, 449, 578, 668, 669, 816, 825, 840, 841

[56] References Cited

U.S. PATENT DOCUMENTS

| | | | |
|---|---|---|---|
| 1,334,040 | 3/1920 | Lee | 439/825 |
| 2,702,376 | 2/1955 | Brush | 439/669 |
| 3,264,597 | 8/1966 | Gammel, Sr. | 439/825 |
| 3,289,149 | 11/1966 | Pawloski | 439/669 |
| 4,112,953 | 9/1978 | Shanker et al. | 128/419 P |

Primary Examiner—Randall L. Green
Assistant Examiner—Randy Shay
Attorney, Agent, or Firm—Flehr, Hohbach, Test, Albritton & Herbert

[57] ABSTRACT

A guide wire assembly comprising a flexible guide wire having a diameter of 0.018 inches or less and having a connector assembly. The connector assembly includes male and female connectors. The male connector includes a conductive coil spring and a core wire which extends beyond the conductive coil. The female connector includes a recess for receiving the core wire as well as a conductive element for engaging the coil spring.

9 Claims, 2 Drawing Sheets

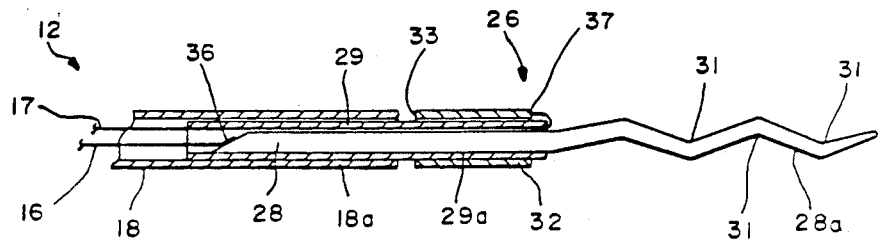
FIG.—1
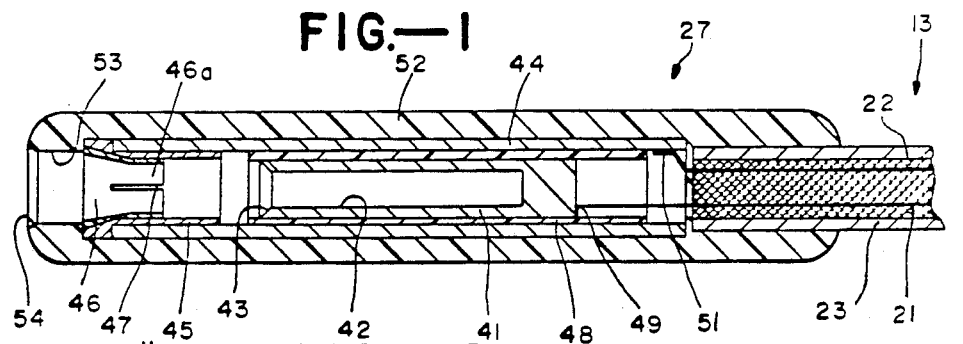
FIG.—2
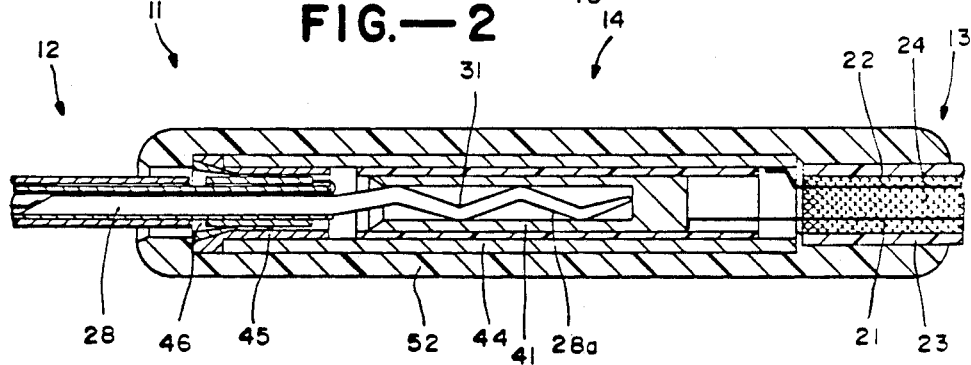
FIG.—3
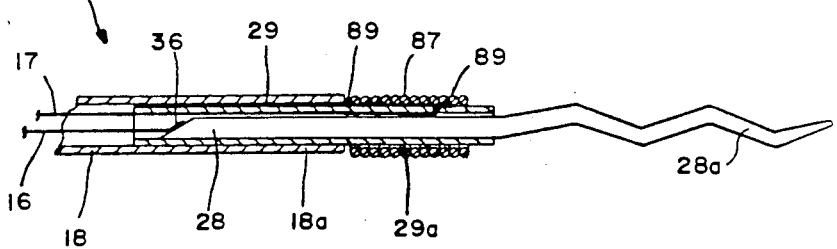
FIG.—7

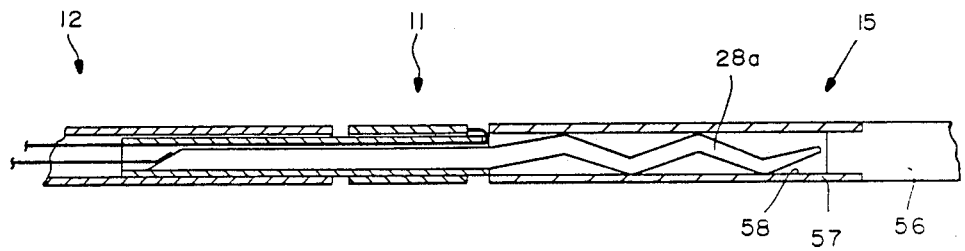
FIG.—4
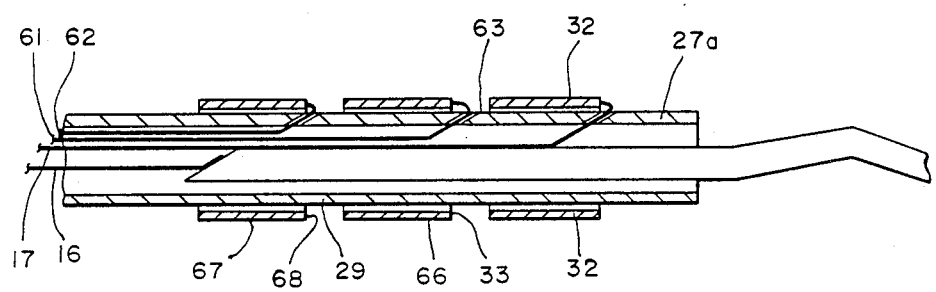
FIG.—5
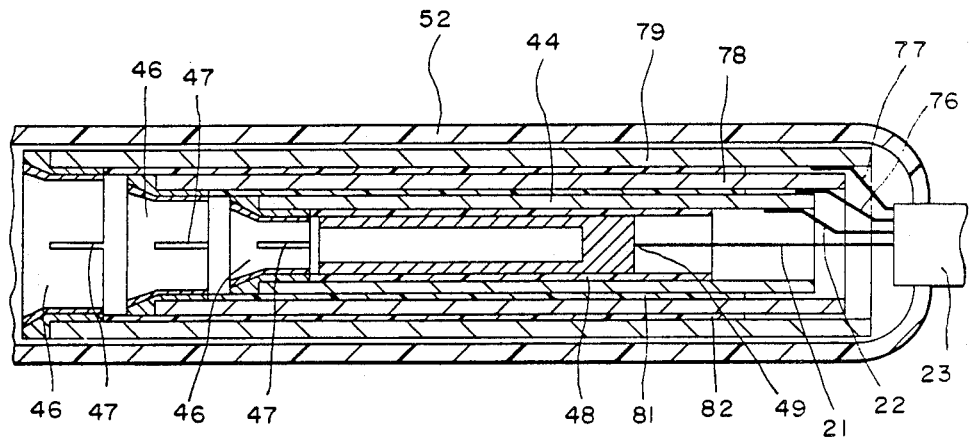
FIG.—6 ns with an electrical function and connectors for use therewith and more particularly, such a guide wire assembly with

GUIDE WIRE ASSEMBLY WITH ELECTRICAL FUNCTIONS AND MALE AND FEMALE CONNECTORS FOR USE THEREWITH

This invention relates to a guide wire assembly with electrical function and connectors for use therewith and more particularly, such a guide wire assembly with male and female connectors. This application is a continuation-in-part of application Ser. No. 265,909 filed on Nov. 2, 1988.

Heretofore there has been developed by Advanced Cardiovascular Systems, Inc. and placed on the market a detachable-on-command guide wire system which utilizes a guide wire with a detachable extension guide wire. This detachable-on-command system utilizes a connector which was comprised of a metallic sleeve into which was fitted a crimped core wire in order to achieve the desired amount of frictional engagement between the guide wire and the extension wire.

A guide wire has been developed as disclosed in copending application Ser. No. 036,796 filed Apr. 10, 1987 in which a transducer is carried at the end of a guide wire for making Doppler blood flow measurements which requires the use of first and second conductors extending the length of the guide wire. With such a guide wire a situation may arise where it will be desirable to utilize an extension guide wire to make possible exchange procedures often used in angioplasty. At the present time such exchange procedures are not possible because the connectors and guide wires utilized heretofore do not have conductive functions incorporated therein.

There is therefore a need for a guide wire assembly with an electrical function which includes male and female connectors which can be utilized with guide wires and extension wires.

In general, it is an object of the invention to provide a guide wire assembly with an electrical function.

Another object of the invention is to provide a guide wire assembly of the above character in which the assembly includes male and female connectors.

Another object of the invention is to provide a guide wire assembly of the above character in which two or more conductors can be provided.

Another object of the invention is to provide a guide wire assembly of the above character which is compatible with the existing guide wire exchange systems.

Another object of the invention is to provide male and female connectors of the above character which are compatible in size with existing guide wires. Another object of the invention is to provide a guide wire assembly of the above character in which the assembly has been provided with stress relief features.

Additional objects and features of the invention will appear from the following description in which the preferred embodiments are set forth in detail in conjunction with the accompanying drawings.

FIG. 1 is a cross-sectional view of a micro-miniature co-axial connector for use on guide wire assembly having an electrical function.

FIG. 2 is a cross-sectional view of a micro-miniature co-axial female connector for use on guide wire assembly having an electrical function.

FIG. 3 is a cross-sectional view showing the male mating positions.

FIG. 4 is a cross-sectional view of the male connector of the present invention mated with a female connector of a conventional extension wire.

FIG. 5 is a cross-sectional view of a male connector similar to that in FIG. 1, but with additional conductors.

FIG. 6 is a cross-sectional view of a female connector similar to that in FIG. 2 with additional conductors.

FIG. 7 is a cross sectional view of a micro miniature co-axial connector for use on a guide wire assembly of the type shown in FIG. 1 which incorporates strain relief capabilities.

In general, the guide wire assembly of the present invention is comprised of a guide wire having first and second conductors extending along the length thereof, an extension guide wire and a conducting cable. Connector means is provided for connecting the conducting cable or alternatively the extension guide wire to the guide wire and interconnecting the conductors carried thereby. The connector means includes a male connector having a metallic sleeve, a conductive core mounted in the sleeve and extends forwardly to provide a conductive probe. Insulating material separates the conductive core from the sleeve. The insulating material extends forwardly of the sleeve. A conductive band is carried by the insulating material and is spaced from the sleeve. First and second conductors are disposed in the sleeve with the first conductor being connected to the conductive core and the second conductor being connected to the conductive band. A female connector is provided for the conducting cable. The female connector is provided with an inner conductive grip which has a cylindrical recess for receiving the conductive probe of the male connector. The female connector is also provided with an outer conductive grip which has a cylindrical engaging portion extending forwardly of the inner conductive grip. Insulating means is disposed between the inner and outer conductive grips. An insulating housing is mounted on the outer conductive grip. First and second conductors are disposed within the housing with the first conductor being connected to the inner conductive grip and the second conductor being connected to the outer conductive grip. The female connector receives the male connector with the conductive grip receiving the conductive probe in the cylindrical recess and the outer conductive grip receiving the cylindrical band to make electrical connections therebetween.

More particularly as shown in the drawings, in FIGS. 1, 2, 3 and 4, the guide wire assembly 11 consists of a guide wire 12 (FIG. 1) and a flexible conducting cable 13 (FIG. 2) which are interconnected by connector means 14 (FIG. 3).

Alternatively, the guide wire 12 can be connected to a conventional extension wire 15 (FIG. 4). The guide wire 12, the conducting cable 13 and the connector means 14 are all provided with conductive functions as hereinafter described. The guide wire 12 can be of the type described in co-pending application Ser. No. 036,796, filed Apr. 10, 1987 which can be provided with a transducer (not shown) on its distal extremity which is provided with first and second conductors 16 and 17 which are connected to the transducer and which extend the length of the guide wire internally of the outer sleeve 18. The other details of the construction of the guide wire 12 are disclosed in said copending application and are not disclosed herein because they are not relevant to the present invention. The flexible conducting cable 13 is also provided with first and second conductors 21 and 22 which extend along the length of the flexible conducting cable 13 and are enclosed in a suitable insulating jacket 23 as, for example, one of plastic. Shielding 24 of a suitable type such as formed by braided metal wire surround the conductors 21 and 22.

The connector means 14 consists of male and female connectors 26 and 27 with the male connector 26 being connected to the guide wire 12 and the female connector being connected to the conducting cable 13. It should be appreciated that the male and female connectors 26 and 27 serve as cooperative mating means and that if desired, the male connector 26 could be connected to the conducting cable 13 and the female connector connected to the guide wire 12.

The male connector 26 is shown in detail in FIG. 1 and consists of a proximal sleeve portion 18a which is a continuation of the sleeve 18 of the guide wire. The sleeve portion 18a has an outside diameter of 0.018 inches or less so that it can be advanced through a conventional angioplasty catheter. It is formed of a suitable material such as stainless steel and has a suitable wall thickness such as 0.002 inches.

A conductive core wire 28 is provided which has its distal extremity disposed within the proximal extremity 18a of the tubing 18. It has a suitable diameter as, for example 0.010 inches. A sleeve 29 of an insulating material extends over the portion of the core wire 28 disposed within the sleeve portion 18a and serves to insulate the core wire 28 from the sleeve 18a. The sleeve 29 can be formed of a suitable material such as a polyimide. Any other suitable thermoplastic material which can be applied can also be utilized for the sleeve. The sleeve 29 is provided with a cylindrical portion 29a which extends proximally to the proximal extremity of the sleeve portion 18a.

The proximal extremity of the core wire 28 is provided with a tapered or probe portion 28a which may be tapered from 0.010 inches down to 0.006 inches. The portion 28a is also crimped as shown to provide a plurality of sharp bends 31 which enhance the frictional fit between the male and female connectors as hereinafter described. The crimped portion is about 1–2 cm long. The conductive cylindrical member in the form of a core wire 28 can be formed of any suitable conductive material as, for example, stainless steel or beryllium copper which are particularly desirable because of their springiness. A conductive cylindrical member in the form of a band 32 is mounted on the proximal extremity of the insulative sleeve 29 but is spaced therefrom to provide a circumferential air gap 33 which, if desired, can be filled with an adhesive (not shown) which also can serve as an insulator. The band 32 can be formed of a suitable conductive material such as beryllium copper. The first conductor 16 is connected to the distal extremity of the core wire 28 by a solder joint 36. The second conductor 17 extends through the insulating sleeve 29 and over the core wire 28 and is connected to the conductive band 32 at a solder joint 37. Thus it can be seen that the conductive core wire 28 serves as one conductor and the conductive band 32 serves as the other conductor. The male connector 26 hereinbefore described is a micro-miniature coaxial connector that is provided with electrical functions which in particular is capable of providing electrical connections between two separate conductors.

The female connector 27 is shown in detail in FIG. 2 and as shown therein consists of an inner conductive grip 41 formed of a suitable material such as beryllium copper and which is provided with a cylindrical recess 42 which can have a diameter ranging from 0.010 to 0.014 inches and preferably has a diameter of approximately 0.012 inches. The recess 42 is open at its forward extremity which is facing towards the distal extremity of the female connector 27. The recess 42 is provided with a chamfer 43 to facilitate the entry of the crimped conductive core wire portion or probe 28a of the male connector 26 as hereinafter described. An outer conductive grip 44 is provided. It consists of a cylindrical sleeve which is disposed coaxially with respect to the inner conductive grip 41. A shouldered sleeve-like insert 45 is mounted by a press fit in the extremity of the sleeve 44 extending beyond the inner conductive grip. A tapered insert 46 is mounted within the insert 45 and is surrounded with six circumferentially spaced slots 47 which are spaced equally and serve to provide spring-like finger portions 46a which are adapted to engage the conductive band 32 carried by the male connector as hereinafter described. The parts of the outer conductive grip 44 are formed of a suitable conducting material such as beryllium copper. A cylindrical sleeve 48 formed of a suitable insulating material such as a polymeric material is disposed between the inner conductive grip 41 and the outer conductive grip 44 to insulate the same from each other. The sleeve 48 can be formed of a polyimide or other electrically insulating material. The first and second conductors 21 and 22 carried by the conducting cable 13 are connected respectively to the inner conductor grip 41 at a crimped joint 49 and to the second or outer conductive grip by a crimped joint 51. An outer molded case 52 formed of an insulating material such as molded plastic is molded over the outer conductive grip 46 and over the distal extremity of the conducting cable 13. The case 52 is provided with a cylindrical opening 53 which is in axial registration with the outer conductive grip 44 and the inner conductive grip 41. The opening 53 is also provided with a chamfer 54.

From the construction shown in FIG. 2 it can be seen that there has been provided a micro-miniature coaxial female connector 27 which can mate with the male connector 26 as shown in FIG. 1. In mating the male connector 26 with the female connector 27, as shown in FIG. 3 the crimped conductive core wire portion or probe 28a is inserted through the opening 53 in the case 52 into the outer conductive grip 44 and into the cylindrical recess 42 provided in the inner conductive grip 41. The conductive probe 28a frictionally engages the cylindrical side wall of the inner conductive grip forming the recess 42. Continued advancement of the conductive probe 28a into the recess 42 brings the conductive band 32 into engagement with the spring fingers 47 so that they frictionally engage the band and make electrical contact with the outer conductive grip at the same time that a connection is being formed by the probe 28a and the inner conductive grip 41. The frictional engagement is such that the guide wire 12 can be advanced and retracted while still maintaining electrical contact with the conducting cable 13 which is connected to the instrumentation being utilized for making flow, pressure or other measurements.

In using the guide wire assembly 11 in connection with an angioplasty procedure, the coronary guide wire would be positioned within an angioplasty catheter to make blood flow measurements before, during and after the angioplasty procedure. Signals would be supplied from the transducer (not shown) provided on the end of the guide wire assembly would be supplied through the connector means 14 to the cable 13 to supply the signal to the electrical console (not shown) to provide the flow measurements. Now let it be assumed that it is desirable to change to a large size or even a smaller size dilatation catheter. When this is the case, the female connector 27 is removed from the male connector 26 carried by the guide wire 12. The guide wire 12 is then ready to be attached to a conventional extension guide wire which has approximately the same length as a guide wire, thus doubling the length of the guide wire to make it possible for the guide wire to remain in place while the dilatation catheter previously being used can be removed from the guide wire and a new dilatation catheter of a different size advanced over the guide wire into the coronary system. The distal extremity of a conventional extension guide wire 15 shown in FIG. 4 in which the guide wire is comprised of a solid stainless steel wire 56 of a suitable outside diameter such as 0.018 inches which has a sleeve 57 also formed of suitable material such as stainless steel bonded to the distal extremity of the same by suitable means such as welding. The sleeve 57 is provided with a cylindrical recess 58 which is adapted to receive the probe 28a of the male connector 26. Thus, although the male connector 26 is provided with a conducting function it still can function in the same manner as a conventional guide wire to mate with the female connector provided on the distal extremity of the exchange wire 15 so that the exchange wire can be utilized to perform its normal function. It can be seen this has been accomplished without increasing the diameter of the male probe which makes it possible to readily make an exchange of dilatation catheters in a manner well known to those skilled in the field of angioplasty.

As soon as the new size catheter is in place, the extension wire can be removed and the micro-miniature female connector 27 can be reattached to the proximal end of the coronary flow guide wire 12 to establish the electrical connection thereto and to again make it possible to monitor blood flow. Thus it can be seen that the present invention makes it possible to provide monitoring of the blood flow without removing the guide wire carrying the transducer while still making it possible to utilize different size dilatation catheters in the angioplasty procedure.

One of the principal advantages of the guide wire assembly of the present invention and in particular the male and female connectors is that they are of a micro-miniature size and make it possible to provide connectors with more than one conductor and which are still capable of being able to be produced in a size which is 0.018 inches in diameter or less.

In the event that it is necessary to provide more than two conductors in a male micro-miniature connector, the same can be accomplished utilizing the same principles which have been utilized in providing the male and female connectors 26 and 27 shown in FIGS. 1 and 2. Thus as shown in FIG. 5, provision can be readily made for additional conductors, as for example, two conductors 61 and 62 which extend through the sleeve 18 and forwardly through the portion 29a of the insulating sleeve 29 extending through holes 63 provided in the insulating sleeve 29 and soldered to additional bands 66 and 67 formed of the same material as band 32 and spaced apart from the band 32 and being spaced apart from each other by a gap 68. Thus it can be seen that four conductors have been provided with the conductive core wire providing the first conductor and the bands 62, 66 and 67 providing the other three conductors. These additional conductors can be provided without increasing the diameter of the male connector. The female connector is augmented in a similar way as shown in FIG. 6 to provide additional conductors as, for example, two additional conductors 76 and 77 which are connected to additional outer conductive grips 78 and 79 which are coaxial with the outer conductive grip 44 and which extend forwardly as shown particularly in FIG. 5 so that they are adapted to engage the additional bands 66 and 67 provided on the male connector. An additional insulating sleeve 81 is provided for electrically isolating the second outer conductive grip 78 from the first outer conductive grip 46 and sleeve 82 is provided for electrically isolating the third outer conductive grip 79 from the second outer conductive grip 78. The case 52 surrounds the outer conductive grip 79.

Operation and use of the connectors shown in FIGS. 5 and 6 is substantially identical to that hereinbefore described. The only additional capability being that additional conductors are provided so that additional electrical functions can be performed by the guide wire. From the foregoing it can be seen that a guide wire assembly and connectors for use therein can be provided which can perform electrical functions and which are of a micro-miniature size so that they can be utilized in conjunction with conventional angioplasty catheters and exchange wires. In order to reduce size, coaxial construction has been utilized for both of the male and female connectors.

An additional embodiment of the invention is shown in the guide wire assembly 86 shown in FIG. 7 which is substantially identical to the guide wire 12 shown in FIG. 1 with the exception that a conductive coil 87 has been provided to replace the conductive band 32 shown in FIG. 1. The conductive coil 87 serves as a conductive sleeve and extends over the insulating sleeve 29 and is formed of a suitable conductive material. For example, stainless steel can be utilized in which the wire would have a diameter ranging from 0.002 to 0.003 inches with a maximum outside diameter on the coil of 0.018 inches. The conductive coil can have a suitable length such as 0.080 to 0.160 inches. The coil 87 is secured to the insulating sleeve 29 by a suitable medical grade adhesive 89 of a conventional type. The adhesive should be very strong and should be capable of withstanding sterilization temperature required for medical instruments. In addition, it should have wicking capabilities so that it will travel through capilliary action into the minute gaps between individual coils of the conductive coil 87 and also extend between the coils and the sleeve 29 as well as the space between the end of the sleeve 18 and the beginning of the coil 87. As with the embodiment shown in FIG. 1, the conductor 16 is secured to the core wire 28 at 36 whereas the conductor 17 extends over the core wire 28 and passes through the insulating sleeve 29 and is connected to the conductive coil at 87 by a suitable conducting bond. It should be appreciated that although stainless steel has been selected for the conductive material for the conductive coil 87 because of its high tensile strength providing better stress relief, other conductive materials such as gold alloys, palladium and platinum would be satisfactory.

The guide wires shown in FIG. 7 are used in the same manner as described hereinbefore for the previous embodiments. However, the strain relief coil 87 serves to distribute the stresses created by flexing of the core wire 28 at the proximal extremity of the outer sleeve 18. Thus, although the core wire 28 is of a very small diameter and is very fragile and flimsy, it can withstand the handling by doctors and other medical personnel because of the stress relief capabilities provided by the conductive coil 87 which serves to prevent bending or actually breaking off of the conductive core wire 28 at the termination of the outer sleeve 18. In other words, the conductive coil 87 removes a high stress region at the transition between the stainless steel outer sleeve 18 and the conductive band 32. The conductive coil 87 therefore serves to provide the conductive material provided by the conductive band 32 while at the same time providing the desired strain relief capability or feature. The stresses created are distributed uniformly over the length of the conductive coil.

What is claimed is:

1. In a guide wire assembly, a flexible guide wire having a diameter of 0.018 inches or less and having first and second conductors extending along the length thereof, a flexible cable having first and second conductors extending along the length thereof, and connector means for interconnecting the flexible cable to said guide wire and interconnecting the conductors carried thereby, said connector means including a male connector and a female connector, said male connector comprising a sleeve, a conductive core wire mounted in the sleeve, insulating means mounted din the sleeve and insulating the conductive core wire from the sleeve, a conductive cylindrical coil spring means carried by the insulating means and spaced from the sleeve but being in relatively close proximity to the sleeve for providing stress relief, said core wire extending beyond the conductive cylindrical coil spring, first and second conductors disposed within the sleeve with the first conductor being connected to the conductive core and the second conductor being connected to the conductive cylindrical coil spring means, said female connector comprising an inner conductive grip having a cylindrical recess for receiving the conductive core wire, an outer conductive grip having a cylindrical member engaging portion, insulating means disposed between the inner and outer conductive grips, an insulating case mounted on the outer conductive grip, first and second conductors disposed within the case with the first conductor being connected to the inner conductive grip and the second conductor being connected to the outer conductive grip, the female connector receiving the male connector with the inner conductive grip receiving the conductive core in the cylindrical recess of the inner conductive grip and with the outer conductive grip receiving the conductive member of the male connector by the cylindrical member engaging portion of the outer conductive grip engaging the conductive cylindrical coil spring means.

2. An assembly as in claim 1 wherein said core wire has a crimped extremity.

3. An assembly as in claim 1 wherein the male and female connectors have a co-axial construction.

4. In a guide wire assembly in the form of a tubular member, a guide wire having a diameter of 0.018 inches or less and having a proximal extremity, first and second conductors extending along the length of the tubular member, a male connector connected to the proximal extremity of the guide wire, the male connector comprising a conductive cylindrical coil spring means spaced from but being in relatively close proximity to the tubular member for providing stress relief, a conductive probe extending beyond the coil spring means insulating means insulating the coil spring means from the probe and the tubular member, and means connecting the first and second conductors to the probe and to the coil spring means, respectively.

5. A guide wire as in claim 4 wherein the probe has a proximal extremity which is crimped.

6. A guide wire as in claim 4 together with an exchanging guide wire, the exchange guide wire having a distal extremity, the distal extremity including a sleeve, the sleeve receiving the probe of the male connector so that the guide wire and the exchange guide wire are frictionally interconnected to inhibit separation of the guide wire from the exchange guide wire.

7. In a male connector, an outer cylindrical sleeve having a proxial extremity, a core wire formed of a conducting material and disposed in the outer cylindrical sleeve and extending beyond the proximal extremity so that it is exposed, a cylindrical sleeve formed of insulating material insulating said core wire from said outer cylindrical sleeve and having an end, said cylindrical sleeve of insulating material having a portion thereof extending beyond said proximal extremity of the outer cylindrical sleeve, and a cylindrical coil spring means of conducting material carried by the outer sleeve of insulating material and being spaced from said sleeve but being in close proximity thereto for providing stress relief and first and second conductors disposed interiorly of the outer cylindrical sleeve and means bonding the first conductor to the core wire and the second conductor to the coil spring means.

8. A male connector as in claim 7 wherein the proximal extremity of the core wire is crimped.

9. A male connector as in claim 7 wherein said coil is formed of stainless steel.

* * * * *

UNITED STATES PATENT AND TRADEMARK OFFICE
CERTIFICATE OF CORRECTION

PATENT NO. : 4,958,642

DATED : September 25, 1990

INVENTOR(S) : Jeffrey J. Christian, et al.

It is certified that error appears in the above-identified patent and that said Letters Patent is hereby corrected as shown below:

At column 7, line 30, Cancel "din" and Substitute therefor --in--

At column 8, line 25, Cancel "ex-changing" and Substitute therefor --exchange--.

Signed and Sealed this

Twenty-fourth Day of August, 1993

Attest:

BRUCE LEHMAN

*Attesting Officer*  *Commissioner of Patents and Trademarks*